United States Patent [19]

Warriner

[11] Patent Number: Plant 7,508

[45] Date of Patent: Apr. 30, 1991

[54] ROSE PLANT JACCART

[75] Inventor: William A. Warriner, Tustin, Calif.

[73] Assignee: Bear Creek Gardens, Inc., Medford, Oreg.

[21] Appl. No.: 478,194

[22] Filed: Feb. 9, 1990

[51] Int. Cl.[5] ..... A01H 5/00

[52] U.S. Cl. ..... Plt./7

[58] Field of Search ..... Plt. 7

*Primary Examiner*—James R. Feyrer

*Attorney, Agent, or Firm*—Klarquist, Sparkman, Campbell, Leigh & Whinston

[57] ABSTRACT

A miniature rose variety having ease of propagation on its own roots from soft wood cuttings, with white flowers edged in red, vigorous upright growth, dwarf habit, resistance to powdery mildew and rust, and excellent recurrent bloom.

1 Drawing Sheet

This present invention relates to a new and distinct variety of rose plant named Jaccart of the miniature class which was originated by me by crossing the variety Libby with an unnamed seedling.

The primary objective of this breeding was to produce a new rose variety having strong vigorous growth, dwarf habit and a red and white flower color. The objective was substantially achieved along with other desirable improvements as evidenced by the following unique combination of characteristics which are outstanding in the new variety and which distinguish it from its parents as well as from all other varieties of which I am aware:

1. White flowers edged in red.
2. Vigorous upright growth, dwarf habit.
3. Resistance to powdery mildew and rust.
4. Excellent recurrent bloom.
5. Ease of propagation on its own roots from soft wood cuttings.

Asexual reproduction of this new variety by rooting of soft wood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Libby.

*Pollen parent.*—An unnamed seedling.

Classification:

*Botanical.*—*Rosa hybrida.*

*Commercial.*—Miniature.

FLOWER

Observations made from specimens grown in a garden in Somis, Calif. from June to October, 1989.

Blooming habit: Recurrent.

Bud:

*Size.*—½ inch when the petals start to unfurl.

*Form.*—Short, pointed ovoid.

*Color.*—When sepals first divide: White Group 155D edged in Red Group 46B. When half blown: The upper sides of the petals are White Group 155D edged in Red Group 46B; and the lower sides of the petals are mostly White Group 155D edged in Red Group 46B.

*Sepals.*—Color: Green Group 138B. Surface texture: Covered in fine hairs and occasional glands. Three normally appendaged sepals and two unappendaged sepals with hairy edges.

*Receptacle.*—Color: Green Group 138B. Shape: Funnel. Size: Small. Surface: Smooth.

*Peduncle.*—Medium: Surface: Smooth. Color: Light green. Strength: Stiff, erect.

Bloom:

*Size.*—Small. Average open size is 1 to 1¼ inches.

*Borne.*—Singly.

*Stems.*—Short, strong.

*Form.*—When first open: High centered. Permanence: Flattens, outer petal edges curl slightly.

*Petalage.*—Number of petals under normal conditions: 40–50.

*Color.*—Upper side of petals is White Group 155D edged in Red Group 46B with the red confined to petal edges. Reverse side of petals is same. Base of petals is very small greenish-white half moon at point of attachment. Major color on the upper side is White Group 155D edged in Red Group 46B.

*Variegations.*—None.

*Discoloration.*—General tonality at end of first day: None; at the end of the third day: Color of the red fades to Red Group 46D.

*Fragrance.*—None.

Petals:

*Texture.*—Thin.

*Shape.*—Oval.

*Form.*—Tips slightly recurved, edges slightly quilled.

*Arrangement.*—Imbricated. Petaloids in the center: Few.

*Persistence.*—Drop off cleanly.

*Lastingness.*—On the plant: Fair. As a cut flower: Fair.

Reproductive parts:

*Anthers.*—Size: Small. Quantity: Few. Color: Yellow. Arrangement: Regular around sides, mixed with petaloids.

*Filaments.*—Color: White.

*Pollen.*—Color: Lemon Yellow.

*Styles.*—Color: Red.

*Stigmas.*—Color: Greenish white.

Form: Bush.

Growth: Vigorous, dwarf, upright.

Foliage:

*Number of leaflets on normal mid-stem leaves.*—5.

*Size.*—Small.

*Quantity.*—Normal.

*Color.*—New foliage: Bronze-red. Old foliage: Dark glossy green.

Leaflets:

*Shape.*—Pointed oval.

*Texture.*—Glossy, smooth.

*Edge.*—Serrated.

*Serration.*—Single, small.

*Petiole.*—Rachis: Reddish. Underside: Rough, with prickles.

*Stipules.*—Long to medium, serrated.

*Disease resistance.*—Resistant to powdery mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Short, hooked slightly downward.

*Color when young.*—Red.

Small prickles:

*Quantity.*—On main stalks: None. On laterals: None.

I claim:

1. A new and distinct variety of rose plant of the miniature class, substantially as herein shown and described, characterized particularly as to novelty by the unique combination of its ability to propagate easily from soft wood cuttings, near continuous bloom during the growing season, novel white edged with red blooms, resistance to disease and its dwarf but vigorous habit of growth.

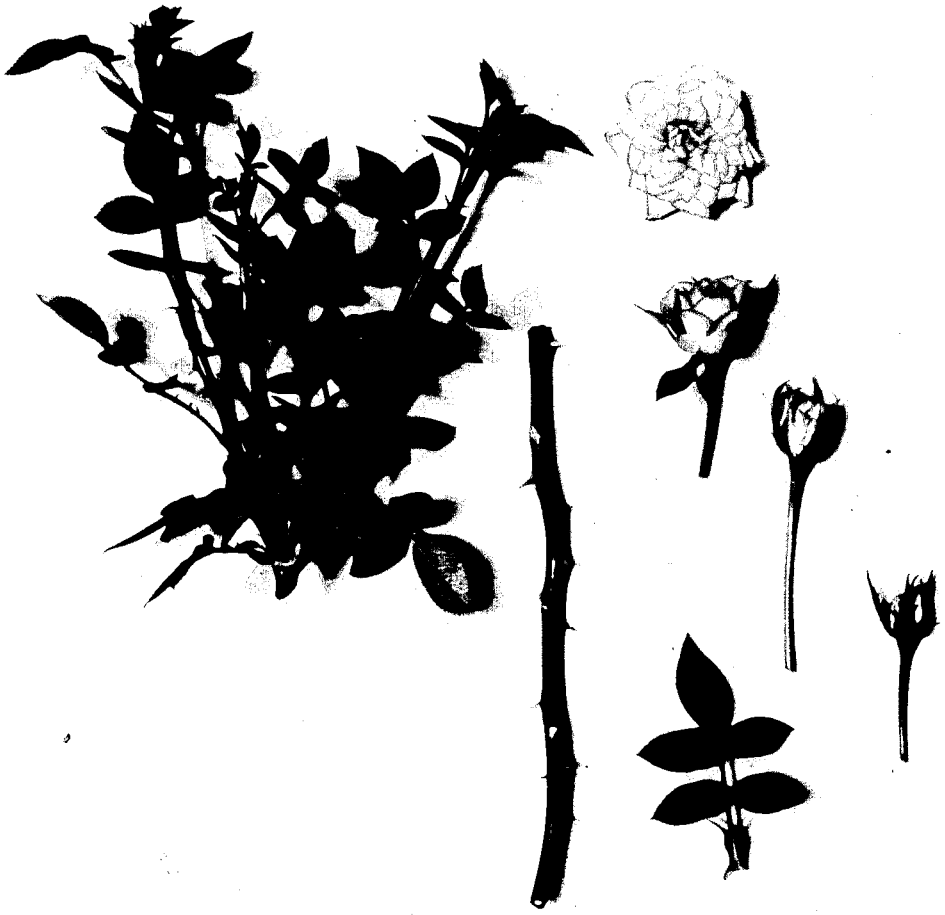

* * * * *